(12) United States Patent
Li

(10) Patent No.: US 8,903,490 B2
(45) Date of Patent: Dec. 2, 2014

(54) METHODS AND SYSTEMS FOR RECOGNIZING ARRHYTHMIAS USING NEURAL STIMULATION

(75) Inventor: Dan Li, Shoreview, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 299 days.

(21) Appl. No.: 13/019,868

(22) Filed: Feb. 2, 2011

(65) Prior Publication Data

US 2011/0218586 A1 Sep. 8, 2011

Related U.S. Application Data

(60) Provisional application No. 61/310,002, filed on Mar. 3, 2010.

(51) Int. Cl.
*A61N 1/00* (2006.01)
*A61N 1/365* (2006.01)

(52) U.S. Cl.
CPC ..................................... *A61N 1/365* (2013.01)
USPC ..................................... 607/14; 607/4; 607/5

(58) Field of Classification Search
CPC . A61N 1/365; A61N 1/36114; A61N 1/3621; A61N 1/37
USPC .......................... 607/4–6, 9, 14; 600/515–518
See application file for complete search history.

(56) References Cited

U.S. PATENT DOCUMENTS

| | | | |
|---|---|---|---|
| 5,107,850 A * | 4/1992 | Olive | .................. 600/518 |
| 5,243,980 A | 9/1993 | Mehra | |
| 5,330,507 A | 7/1994 | Schwartz | |
| 5,334,221 A | 8/1994 | Bardy | |
| 5,356,425 A | 10/1994 | Bardy et al. | |
| 5,411,531 A | 5/1995 | Hill et al. | |
| 5,507,784 A | 4/1996 | Hill et al. | |
| 5,713,924 A | 2/1998 | Min et al. | |
| 6,178,350 B1 * | 1/2001 | Olson et al. | .................. 607/4 |
| 6,272,377 B1 | 8/2001 | Sweeney et al. | |

(Continued)

FOREIGN PATENT DOCUMENTS

| | | |
|---|---|---|
| EP | 0547734 A2 | 6/1993 |
| WO | WO-2006107578 A2 | 10/2006 |

OTHER PUBLICATIONS

Lazzara, R., et al., "Selective in situ parasympathetic control of the canine sinoatrial and atrioventricular nodes", Circ Res., 32(3), (Mar. 1973), 393-401.

(Continued)

*Primary Examiner* — Catherine Voorhees
(74) *Attorney, Agent, or Firm* — Schwegman Lundberg & Woessner, P.A.

(57) ABSTRACT

In various method embodiments for classifying an arrhythmia, a characteristic of a ventricle is sensed before delivering a diagnostic neural stimulation. The diagnostic neural stimulation is delivered, and the characteristic of the ventricle is sensed while delivering the diagnostic neural stimulation. The sensed characteristic of the ventricle before and during the diagnostic neural stimulation is used to classify the arrhythmia as either a supraventricular tachyarrhythmia (SVT) or a ventricular tachycardia (VT). According to various embodiments, the characteristic of the ventricle is ventricular rate, similarity values of sensed ventricular morphology to a normal sinus rhythm (NSR), or ventricular hemodynamics. Various embodiments use ventricular rate regularity before and during the diagnostic neural stimulation to classify an SVT as atrial fibrillation (AF) or as another SVT.

22 Claims, 8 Drawing Sheets

(56) References Cited

U.S. PATENT DOCUMENTS

| | | |
|---|---|---|
| 6,292,695 B1 | 9/2001 | Webster, Jr. et al. |
| 7,218,964 B2 | 5/2007 | Hill et al. |
| 7,245,967 B1 | 7/2007 | Shelchuk |
| 7,277,761 B2 | 10/2007 | Shelchuk |
| 7,480,529 B2 | 1/2009 | Li |
| 7,555,341 B2 | 6/2009 | Moffitt et al. |
| 8,195,281 B2 * | 6/2012 | Dal Molin et al. ............. 600/518 |
| 8,233,982 B2 * | 7/2012 | Libbus ............................ 607/14 |
| 2002/0026222 A1 | 2/2002 | Schauerte et al. |
| 2002/0193696 A1 | 12/2002 | Hsu et al. |
| 2003/0060849 A1 | 3/2003 | Hsu |
| 2003/0074026 A1 | 4/2003 | Thompson et al. |
| 2003/0144700 A1 | 7/2003 | Brown et al. |
| 2004/0073098 A1 | 4/2004 | Geva et al. |
| 2004/0093035 A1 | 5/2004 | Schwartz et al. |
| 2004/0116972 A1 | 6/2004 | Marcovecchio |
| 2005/0021097 A1 | 1/2005 | Thompson et al. |
| 2005/0149125 A1 | 7/2005 | Kim et al. |
| 2005/0159781 A1 | 7/2005 | Hsu et al. |
| 2005/0256544 A1 | 11/2005 | Thompson |
| 2005/0261744 A1 | 11/2005 | Li |
| 2006/0111643 A1 | 5/2006 | Cazares et al. |
| 2006/0122527 A1 | 6/2006 | Marcovecchio |
| 2006/0136002 A1 | 6/2006 | Sheth et al. |
| 2006/0161069 A1 | 7/2006 | Li |
| 2006/0224202 A1 | 10/2006 | Moffitt et al. |
| 2006/0281998 A1 | 12/2006 | Li |
| 2007/0142866 A1 | 6/2007 | Li |
| 2007/0173894 A1 | 7/2007 | Li |
| 2007/0179543 A1 | 8/2007 | Ben-David et al. |
| 2007/0197928 A1 | 8/2007 | Kim et al. |
| 2007/0249945 A1 | 10/2007 | Li et al. |
| 2007/0260283 A1 | 11/2007 | Li |
| 2007/0276276 A1 | 11/2007 | Cao et al. |
| 2007/0282380 A1 | 12/2007 | Brooke et al. |
| 2007/0293894 A1 | 12/2007 | Zhang et al. |
| 2008/0015651 A1 | 1/2008 | Ettori et al. |
| 2008/0015659 A1 * | 1/2008 | Zhang et al. .................... 607/62 |
| 2008/0086175 A1 * | 4/2008 | Libbus et al. .................... 607/5 |
| 2008/0177340 A1 | 7/2008 | Kim et al. |
| 2008/0183228 A1 | 7/2008 | Kim et al. |
| 2008/0262558 A1 | 10/2008 | Dong et al. |
| 2008/0269819 A1 * | 10/2008 | Zhou ............................... 607/14 |
| 2008/0281367 A1 | 11/2008 | Zhang et al. |
| 2009/0005826 A1 | 1/2009 | Li |
| 2009/0005828 A1 | 1/2009 | Levine |
| 2009/0036940 A1 | 2/2009 | Wei et al. |
| 2009/0099616 A1 | 4/2009 | Li et al. |
| 2009/0118630 A1 | 5/2009 | Li |
| 2009/0157133 A1 | 6/2009 | Perschbacher et al. |
| 2009/0198294 A1 * | 8/2009 | Rossing et al. ................... 607/4 |
| 2009/0234211 A1 | 9/2009 | Li et al. |
| 2009/0234408 A1 | 9/2009 | Moffitt et al. |
| 2009/0240300 A1 | 9/2009 | Lian et al. |
| 2009/0254135 A1 | 10/2009 | Shuros et al. |
| 2009/0254137 A1 | 10/2009 | Salo et al. |
| 2009/0259269 A1 | 10/2009 | Brown |
| 2009/0264716 A1 | 10/2009 | Shuros et al. |
| 2009/0264946 A1 | 10/2009 | Doerr et al. |
| 2009/0264947 A1 | 10/2009 | Doerr et al. |
| 2009/0287268 A1 | 11/2009 | Nabutovsky et al. |
| 2009/0292332 A1 | 11/2009 | Li et al. |
| 2009/0306486 A1 | 12/2009 | Li et al. |
| 2009/0306731 A1 | 12/2009 | Doerr |
| 2009/0312811 A1 * | 12/2009 | Hsu .................................. 607/4 |
| 2010/0036447 A1 * | 2/2010 | Zhang et al. ..................... 607/4 |
| 2010/0049267 A1 | 2/2010 | Mollerus |
| 2010/0106036 A1 | 4/2010 | Dong et al. |
| 2010/0114212 A1 | 5/2010 | Doerr et al. |
| 2010/0114213 A1 | 5/2010 | Doerr |
| 2010/0174206 A1 | 7/2010 | Kamousi et al. |
| 2010/0198285 A1 | 8/2010 | Rom |
| 2010/0249626 A1 | 9/2010 | El Arab et al. |
| 2010/0249627 A1 | 9/2010 | Zhang et al. |
| 2010/0262030 A1 | 10/2010 | Kim et al. |
| 2010/0268290 A1 | 10/2010 | Li |
| 2010/0274148 A1 | 10/2010 | Zhang et al. |
| 2010/0280841 A1 | 11/2010 | Dong et al. |

OTHER PUBLICATIONS

Schauerte, P., et al., "Ventricular rate control during atrial fibrillation by cardiac parasympathetic nerve stimulation: a transvenous approach", J Am Coll Cardiol., 34(7), (Dec. 1999), 2043-50.

Wallick, D W, et al., "Selective AV nodal vagal stimulation improves hemodynamics during acute atrial fibrillation in dogs", American Journal of Physiology—Heart & Circulatory Physiology, 281(4), (Oct. 2001), H1490-7.

Wen, Zu-Chi, et al., "Electrophysiological mechanisms and determinants of vagal maneuvers for termination of paroxysmal supraventricular tachycardia.", Circulation, 98(24), (Dec. 15, 1998), 2716-23.

Zhuang, S., et al., "Ventricular rate control by selective vagal stimulation is superior to rhythm regularization by atrioventricular nodal ablation and pacing during atrial fibrillation.", Circulation, 106(14), (Oct. 1, 2002), 1853-8.

* cited by examiner

METHODS AND SYSTEMS FOR RECOGNIZING ARRHYTHMIAS USING NEURAL STIMULATION

CLAIM OF PRIORITY

This application claims the benefit of priority under 35 U.S.C. §119(e) of U.S. Provisional Patent Application Ser. No. 61/310,002, filed on Mar. 3, 2010, which is herein incorporated by reference in its entirety.

TECHNICAL FIELD

This application relates generally to medical systems and, more particularly, to systems, devices and methods for recognizing cardiac arrhythmias.

BACKGROUND

The heart is the center of a person's circulatory system. The left portions of the heart draw oxygenated blood from the lungs and pump it to the organs of the body to provide the organs with their metabolic needs for oxygen. The right portions of the heart draw deoxygenated blood from the body organs and pump it to the lungs where the blood gets oxygenated. Contractions of the myocardium provide these pumping functions. In a normal heart, the sinoatrial node, the heart's natural pacemaker, generates electrical impulses that propagate through an electrical conduction system to various regions of the heart to excite the myocardial tissues of these regions. Coordinated delays in the propagations of the electrical impulses in a normal electrical conduction system cause the various portions of the heart to contract in synchrony, which efficiently pumps the blood. Blocked or abnormal electrical conduction or deteriorated myocardial tissue causes dyssynchronous contraction of the heart, resulting in poor hemodynamic performance, including a diminished blood supply to the heart and the rest of the body. Heart failure occurs when the heart fails to pump enough blood to meet the body's metabolic needs.

Tachyarrhythmias are abnormal heart rhythms characterized by a rapid heart rate. Examples of tachyarrhythmias include supraventricular tachycardias (SVT's) such as atrial tachycardia (AT), and atrial fibrillation (AF), and the more dangerous ventricular tachyarrhythmias which include ventricular tachycardia (VT) and ventricular fibrillation (VF). Abnormal ventricular rhythms occur when re-entry of a depolarizing wavefront in areas of the ventricular myocardium with different conduction characteristics becomes self-sustaining or when an excitatory focus in the ventricle usurps control of the heart rate from the sinoatrial node. The result is rapid and ineffective contraction of the ventricles out of electromechanical synchrony with the atria. Most abnormal ventricular rhythms exhibit an abnormal QRS complex in an electrocardiogram because the depolarization spreads from the excitatory focus or point of re-entry directly into the myocardium rather than through the normal ventricular conduction system. Ventricular tachycardia is typically characterized by distorted QRS complexes that occur at a rapid rate, while ventricular fibrillation is diagnosed when the ventricle depolarizes in a chaotic fashion with no identifiable QRS complexes. Both ventricular tachycardia and ventricular fibrillation are hemodynamically compromising, and both can be life-threatening. Ventricular fibrillation, however, causes circulatory arrest within seconds and is the most common cause of sudden cardiac death.

Cardioversion, an electrical shock delivered to the heart synchronously with the QRS complex, and defibrillation, an electrical shock delivered without synchronization to the QRS complex, can be used to terminate most tachyarrhythmias. The electric shock terminates the tachyarrhythmia by simultaneously depolarizing the myocardium and rendering it refractory. A class of cardiac rhythm management (CRM) devices known as implantable cardioverter defibrillators (ICDs) provide this kind of therapy by delivering a shock pulse to the heart when the device detects tachyarrhythmias. Another type of electrical therapy for tachycardia is anti-tachycardia pacing (ATP). In ventricular ATP, the ventricles are competitively paced with one or more pacing pulses in an effort to interrupt the reentrant circuit causing the tachycardia. Modern ICDs typically have ATP capability, and deliver ATP therapy or a shock pulse when a tachyarrhythmia is detected.

Cardioversion/defibrillation consumes a relatively large amount of stored power from the battery and can cause patient discomfort. It is desirable, therefore, to terminate a tachyarrhythmia whenever possible without using shock therapy. Devices have therefore been programmed to use ATP to treat lower rate tachycardias and to use cardioversion/defibrillation shocks to terminate fibrillation and certain high rate tachycardias.

SUMMARY

In various method embodiments for classifying an arrhythmia, a characteristic of a ventricle is sensed before delivering a diagnostic neural stimulation that slows atrioventricular (AV) conduction. The diagnostic neural stimulation to slow AV conduction is delivered, and the characteristic of the ventricle is sensed while delivering the diagnostic neural stimulation. The sensed characteristic of the ventricle before and during the diagnostic neural stimulation is used to classify the arrhythmia as either a supraventricular tachyarrhythmia (SVT) or a ventricular tachycardia (VT). According to various embodiments, the ventricular rate before and during the diagnostic neural stimulation is used to classify the arrhythmia as either the SVT or the VT. According to various embodiments, similarity values of sensed ventricular morphology, both before and during the neural stimulation, to a normal sinus rhythm (NSR) is used to classify the arrhythmia as either the SVT or the VT. According to various embodiments, ventricular hemodynamics before and during the neural stimulation are used to classify the arrhythmia as either the SVT or the VT. Various embodiments use ventricular rate regularity before and during the diagnostic neural stimulation to classify an SVT as atrial fibrillation (AF) or as another SVT.

Various system embodiments for classifying an arrhythmia comprises an arrhythmia discriminator, a neural stimulator, and a controller. The arrhythmia discriminator is configured to discriminate between ventricular tachycardia (VT) and supraventricular tachycardia (SVT). The neural stimulator is configured to generate a neural stimulation signal and deliver the neural stimulation signal to an autonomic neural target. The controller is operably connected to the arrhythmia discriminator and the neural stimulator. The controller is configured to control the neural stimulator to deliver a diagnostic neural stimulation, and to classify the arrhythmia as either the SVT or the VT based on a ventricle characteristic before the diagnostic neural stimulation and a ventricle characteristic during the diagnostic neural stimulation.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
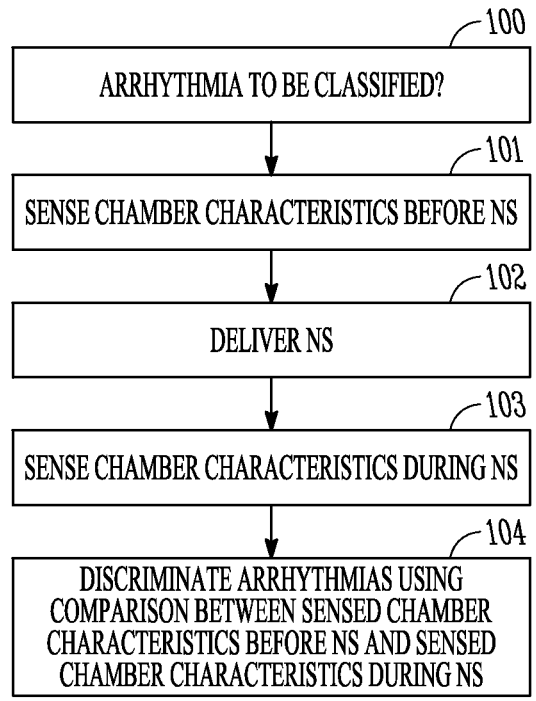
FIG. 1 illustrates an embodiment of a method for using neural stimulation to discriminate between or among different types of arrhythmias.

Supraventricular tachyarrhythmias (SVTs) occur in regions of the heart other than the ventricles, and can originate in either the atrioventricular (AV) node or at a location in the atria. SVTs can be less likely than VT or VF to result in patient death. However, SVTs can still result in significant patient discomfort and elevated stroke risk. SVTs can be relatively common in patients suffering from heart disease.

Examples of SVTs include atrial flutter (AFL), atrial fibrillation (AF), atrioventricular reciprocating tachycardia (AVRT), and AV-nodal reentrant tachycardia (AVNRT). A sinus tachycardia (ST) is a fast heartbeat caused by rapid firing of the SA node.

AFL can be associated with a rapid atrial contraction rate, for example, up to approximately 250-350 beats-per-minute (BPM). Atrial flutter can be associated with the formation of one or more "circus" pathways around the atrium, with the resulting atrial tissue activations occurring at a far higher rate than as directed by the SA node. During an episode of atrial flutter, the AV node can inhibit the transmission of impulses associated with the high atrial contraction rate, resulting in a lower rate of ventricular contractions (e.g., the observed ventricular rate can be below the atrial rate).

AVRT can be similar to atrial flutter, but can involve a reentrant circuit following both a normal conduction pathway between the atria and the ventricles, as well as an abnormal accessory pathway to complete the circuit. AVNRT can be similar to AVRT, but can involve the reentrant circuit following a path through or near the AV node, as well as an accessory path to complete the circuit. Both AVRT and AVNRT can exhibit either antegrade (e.g., normal or "forward" conduction) or retrograde conduction (e.g., depolarization travels opposite its normal direction) through the normal path.

If multiple uncoordinated pathways form, and a predominant reentrant circuit can be absent, AF can be occurring. Unlike VF, AF need not be life threatening since the AV node can block conduction of high-rate uncoordinated atrial events. The resulting intrinsic ventricular contractile behavior can provide adequate hemodynamic margin to sustain the life of the patient.

Discrimination between VT, VF, and SVTs can allow a cardiac rhythm management (CRM) system or health care practitioner to provide life-critical VT or VF therapy when needed. Identifying an arrhythmia as a type of SVT, rather than as VT or VF, can reduce the likelihood of administering a painful and potentially ineffective shock to a conscious patient. In the case of an implantable battery-powered CRM device, reducing inappropriate shocks can also extend battery life, thereby increasing the time before explant and replacement is needed, with its accompanying risks, including infection.

Discrimination between various types of SVTs can also be used to select a therapy more likely to terminate or regulate a specific subclass of SVT. For example, if an SVT can be classified as AF, then one or more devices (e.g., an implantable CRM and neural stimulation device) can respond with, for example, neural stimulation, and an optional atrial shock. If an SVT can be classified as AFL, then a device can respond with, for example, neural stimulation, and an optional anti-tachyarrhythmia pacing (ATP) protocol. Thus, when AF and AFL can be distinguished from each other, unnecessary atrial shock therapy can be suppressed.

In various examples, among other things, the present systems or methods can provide a diagnostic neural stimulation protocol at the onset of an arrhythmia such as to elicit a change in a measurable physiological parameter, such as heart rate, heart rate regularity, morphology, and hemodynamics. Cardiac rate, contractility and excitability can be modulated through central nervous system mediated reflex pathways, which can include portions of the sympathetic and parasympathetic components of the autonomic nervous system. For example, baroreceptors and chemoreceptors in the heart, great vessels, and lungs can transmit cardiac activity information through parasympathetic and sympathetic afferent nervous fibers to the central nervous system. Increase of sympathetic afferent activity can trigger reflex sympathetic activation, parasympathetic inhibition, blood vessel constriction, and tachycardia. In contrast, parasympathetic activation can result in bradycardia, blood vessel dilation, and inhibition of vasopressin release.

The balance between the sympathetic and parasympathetic components of the autonomic nervous system can be referred to as the autonomic tone. Decreased parasympathetic or vagal tone can be a factor that can contribute to or cause various cardiac tachyarrhythmias. Vagal nerve stimulation (VNS) may reduce the firing rate of the sinoatrial (SA) node, reduce the conduction velocity in the atrioventricular (AV) node conduction, and lengthen the refractory period. Direct stimulation of an efferent pathway may cause a slower SA rate, longer AV delay and lengthened refractory period. Additionally, these effects may be caused by activating the baroreflex response, which may be activated by stimulating a baroreceptor, chemoreceptor or an afferent pathway. This disclosure refers to "VNS" to refer to electrical or other stimulation that modulates the autonomic nervous system in a manner that lengthens the AV delay. The present subject matter delivers diagnostic VNS to discriminate between or among different types of arrhythmias, because different types of arrhythmias react differently to the lengthened AV delay.

The slower AV conduction has different impacts on SVT episodes and VT episodes. An SVT episode detected in the VT zone responds to VNS by reduced ventricular rate due to prolonged AV node conduction (i.e. slower conduction). However, a VT episode will not be affected by AV node conduction rate because the ventricular refractory period is not changed during parasympathetic nerve stimulation.

An arrhythmia with a rate that is within the VT zone may be VT or an SVT. Various embodiments determine cardiac responses to VNS to discriminate between an SVT episode and a VT episode. Some embodiments discriminate between an SVT episode and a VT episode using only the ventricular response, such as may be performed by a single chamber device. Some embodiments discriminate based on atrial and ventricular responses, such as may be performed by a dual chamber device or a CRT device. Various embodiments monitor electrophysiological responses and/or mechanical/hemodynamic responses.

Various embodiments transvascularly deliver VNS. By way of example and not limitation, stimulation electrodes may be positioned within the superior vena cava (SVC), the coronary sinus (CS) or the right pulmonary artery (RPA) to deliver the VNS. Various embodiments deliver VNS using a nerve cuff or other electrode configuration. Various embodiments stimulate baroreceptors, such as are present on the carotid sinus or aortic arch, or stimulate the nerves coupled with a baroreceptor. The baroreflex may be activated using electrical stimulation, mechanical activation or other modalities. In some embodiments, the stimulation parameters are able to elicit VNS while being subthreshold for excitation of myocardium. By way of example and not limitation, a 20 Hz, 10 V, 50 µs may be suitable to deliver the VNS therapy.

Various embodiments can be implemented using a single chamber device, and some examples are provided below. Multi-chamber devices are also capable of implementing these embodiments for discriminating among arrhythmias. The present subject matter may use intracardiac electrodes to detect ventricular rate, or may use other ways for detecting cardiac activity such as heart sounds and electrocardiograms.

FIG. 1 illustrates an embodiment of a method for using neural stimulation to discriminate between or among different types of arrhythmias. At 100, it is determined that an arrhythmia should be classified. For example, upon detection of a tachyarrhythmia with a rate in a VT zone, some embodiments determine that the tachyarrhythmia should be classified to distinguish a VT from an SVT, etc. At 101, in anticipating of delivering a diagnostic neural stimulation, characteristics of a heart chamber are sensed. For a ventricular chamber, the sensed chamber characteristics may include ventricular rate, ventricular rate regulatory, ventricular morphology, and/or ventricular hemodynamics. The diagnostic neural stimulation is delivered at 102, and the chamber characteristics are sensed at 103 during the neural stimulation. At 104, arrhythmia discrimination is performed using a comparison between sensed chamber characteristics before the neural stimulation and sensed chamber characteristics during the neural stimulation. Various embodiments identify the arrhythmias for diagnosis. Various embodiments implement a therapy to treat the identified arrhythmia.

In an example, SVT and VT can be discriminated by comparing a ventricular rate without neural stimulation to a ventricular rate during neural stimulation. If the V rate is reduced, then the arrhythmia is classified an SVT. If the V rate is not reduced, then the arrhythmia is classified as a VT. In an example, VNS applied during AF increases the RRI from 311±53 ms to 485±76 ms.

Figure 2:
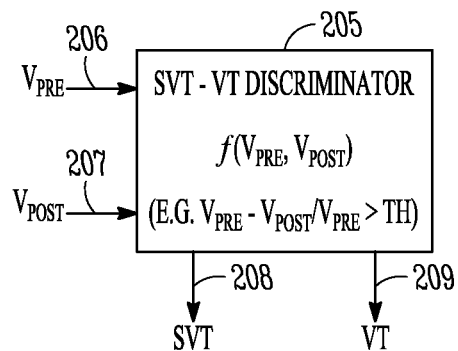
FIG. 2 illustrates an embodiment of a discriminator configured to discriminate between SVT and VT based on ventricular rate.

FIG. 2 illustrates an embodiment of a discriminator configured to discriminate between SVT and VT based on ventricular rate. The illustrated discriminator 205 has two inputs and two outputs. In the illustrated embodiment, a first input 206 provides a ventricular rate before neural stimulation ($V_{PRE}$) and a second input 207 provides a ventricular rate ($V_{POST}$) during neural stimulation. The discriminator performs a function ($f(V_{PRE}, V_{POST})$) based on the ventricular rate to determine if the arrhythmia is an SVT 208 or a VT 209. For example, an embodiment uses the function ($V_{PRE}-V_{POST})/V_{PRE}>TH$. If the ventricular rate is reduced during stimulation by a percentage greater than a programmable threshold, then the arrhythmia is determined to be an SVT. Otherwise, the arrhythmia is determined to be a VT.

Figure 3:
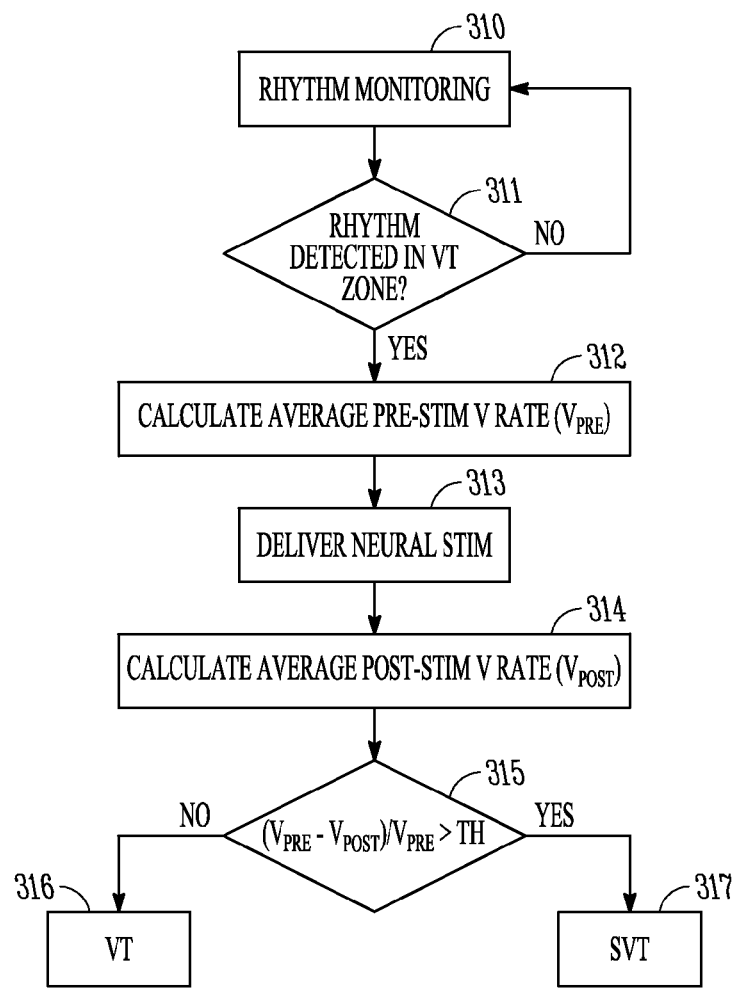
FIG. 3 illustrates an embodiment of a method for using ventricular rate to discriminate between SVT and VT.

FIG. 3 illustrates an embodiment of a method for using ventricular rate to discriminate between SVT and VT. A cardiac rhythm is monitored at 310. If the monitored rhythm is within a VT zone 311, then an average ventricular rate ($V_{PRE}$) is determined at 312 in anticipation for the diagnostic neural stimulation. The diagnostic neural stimulation is delivered at 313, and the average ventricular rate ($V_{POST}$) during the diagnostic neural stimulation is determined at 314. At 315, a discrimination function is applied to the $V_{PRE}$ and $V_{POST}$ to determine if the arrhythmia is a VT 316 or an SVT 317. In an embodiment, the discrimination function is ($V_{PRE}-V_{POST})/V_{PRE}>TH$.

Some embodiments capable of being implemented by a single chamber device discriminate AF from other SVT by comparing ventricular regularity before neural stimulation and ventricular regularity during neural stimulation. When neural stimulation is applied during an AF episode, the reduced AV node conduction is accompanied by an abrupt decrease in regularity of RR intervals during AF (pre-stim 16+/-9% of average ventricular rate, post-stim 27+/-6% of average ventricular rate). AVRT, AVNRT and AT does not experience a significant change in regularity, and are frequently terminated by the neural stimulation. When neural stimulation is applied during an ST episode, the heart rate is gradually slowed, and there is no significant change in regularity. When neural stimulation is applied during an AFL episode, there is no significant change in regularity.

Figure 4:
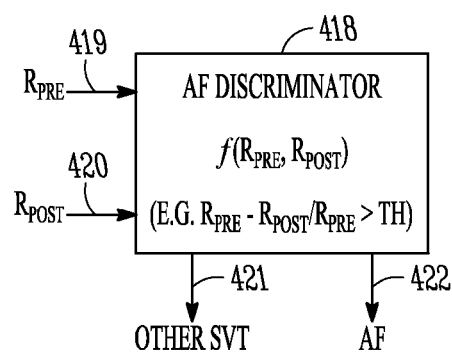
FIG. 4 illustrates an embodiment of a discriminator configured to discriminate between AF and other SVT based on ventricular rate regularity.

FIG. 4 illustrates an embodiment of a discriminator configured to discriminate between AF and other SVT based on ventricular rate regularity. The illustrated discriminator 418 has two inputs and two outputs. In the illustrated embodiment, a first input 419 provides a ventricular rate regularity before neural stimulation ($R_{PRE}$) and a second input 420 provides a ventricular rate regularity ($R_{POST}$) during neural stimulation. The discriminator performs a function ($f(R_{PRE}, R_{POST})$) based on the ventricular rate to determine if the arrhythmia is an AF 422 or another type of SVT 421. For example, an embodiment uses the function ($R_{PRE} - R_{POST})/R_{PRE} > TH$. If the ventricular rate regularity decreases during stimulation by a percentage greater than a programmable threshold, then the arrhythmia is determined to be an AF. Otherwise, the arrhythmia is determined to be another type of SVT.

Figure 5:
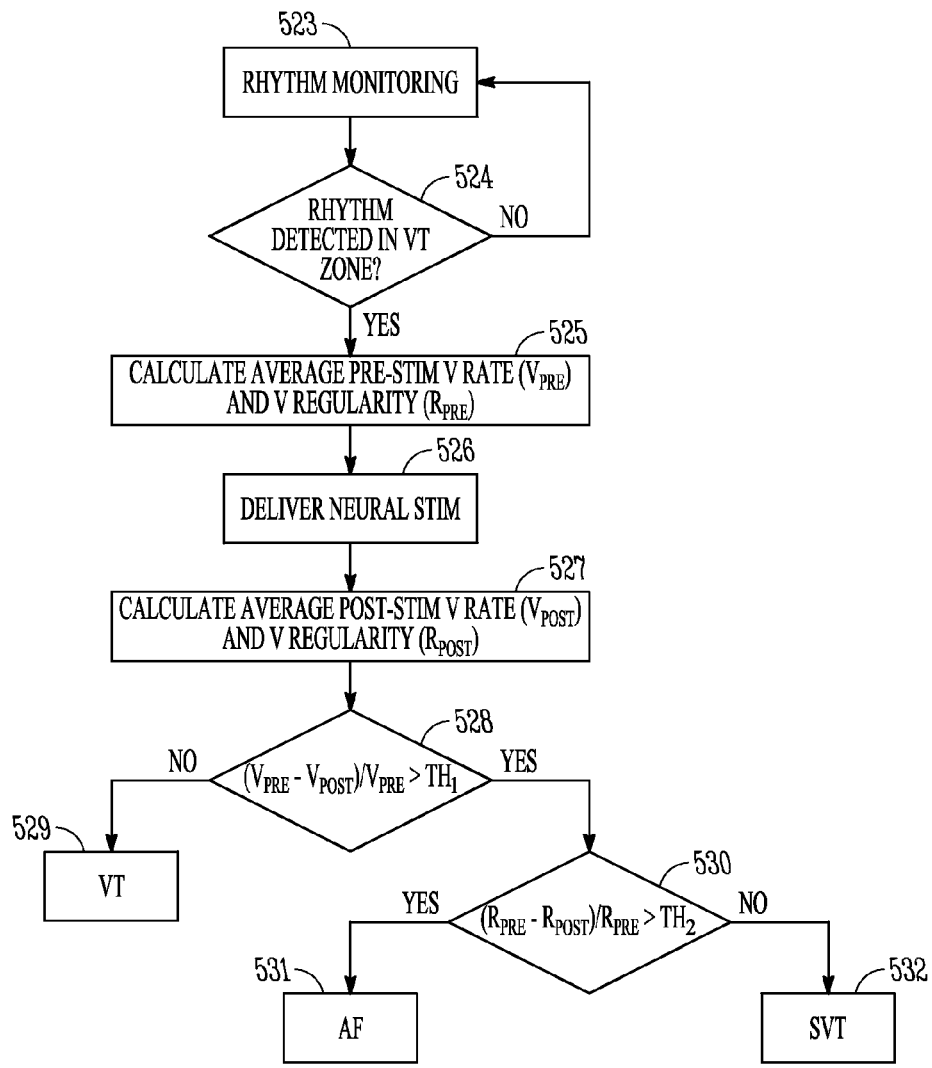
FIG. 5 illustrates an embodiment of a method for using ventricular rate regularity to discriminate between AF and other SVT.

FIG. 5 illustrates an embodiment of a method for using ventricular rate regularity to discriminate between AF and other SVT. A cardiac rhythm is monitored at 523. If the monitored rhythm is within a VT zone 524, then an average ventricular rate ($V_{PRE}$) and ventricular rate regularity ($R_{PRE}$) is determined at 525 in anticipation for the diagnostic neural stimulation. Examples of a regularity measure include signal variance or entropy (see U.S. Pat. No. 7,480,529, entitled "Method and Apparatus For Cardiac Arrhythmia Classification Using Sample Entropy," which is herein incorporated by reference in its entirety. The diagnostic neural stimulation is delivered at 526, and the average ventricular rate ($V_{POST}$) and ventricular rate regularity ($R_{POST}$) during the diagnostic neural stimulation is determined at 527. At 528, a discrimination function is applied to the $V_{PRE}$ and $V_{POST}$ to determine if the arrhythmia is a VT 529. According to various embodiments, the discrimination function is ($V_{PRE} - V_{POST})/V_{PRE} > TH_1$. If the function is not greater than the first threshold $TH_1$, then the arrhythmia is an SVT. At 530, another function ($R_{PRE} - R_{POST})/R_{PRE} > TH$) is applied to the $R_{PRE}$ and $R_{POST}$ to determine if the SVT is an AF 531 or another type of SVT 532.

Some embodiments capable of being implemented by a single chamber device discriminate SVT and VT by comparing ventricular morphology before neural stimulation to ventricular morphology during neural stimulation. Wide QRS tachycardia is the most difficult rhythm to classify. It is a leading cause of false positive detection and inappropriate therapy. Wide QRS could be VT, or SVT with rate-dependent bundle branch block (BBB) or rate aberrancy. Neural stimulation slows down the AV node and AV-His (AH) conduction, and thus may reduce the widening of QRS due to rate-dependent BBB. If morphology similarity between the arrhythmic beats and a pre-stored template improves, then the arrhythmia is classified as an SVT. Otherwise, the arrhythmia is classified as a VT.

Figure 6:
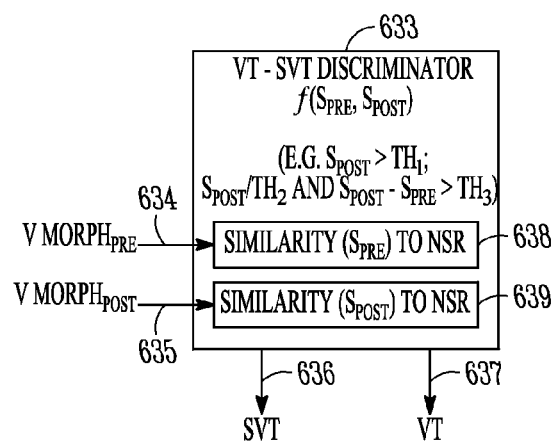
FIG. 6 illustrates an embodiment of a discriminator configured to discriminate between SVT and VT based on ventricular morphology.

FIG. 6 illustrates an embodiment of a discriminator configured to discriminate between SVT and VT based on ventricular morphology. The illustrated discriminator 633 has two inputs and two outputs. In the illustrated embodiment, a first input 634 provides a ventricular morphology before neural stimulation (V $MORPH_{PRE}$) and a second input 635 provides a ventricular morphology (V $MORPH_{POST}$) during neural stimulation. The discriminator performs a function ($f$(V $MORPH_{PRE}$, V $MORPH_{POST}$)) based on the ventricular morphology to determine if the arrhythmia is an SVT 636 or a VT 637. For example, an embodiment compares V $MORPH_{PRE}$ to a normal sinus rhythm (NSR) template to obtain a similarity value ($S_{PRE}$) 638 before the diagnostic neural stimulation, and compares V $MORPH_{POST}$ to the NSR to obtain a similarity value ($S_{POST}$) 639 during the diagnostic neural stimulation. If morphology similarity improves, then the arrhythmia is classified as an SVT. Otherwise, the arrhythmia is classified as a VT.

Figure 7:
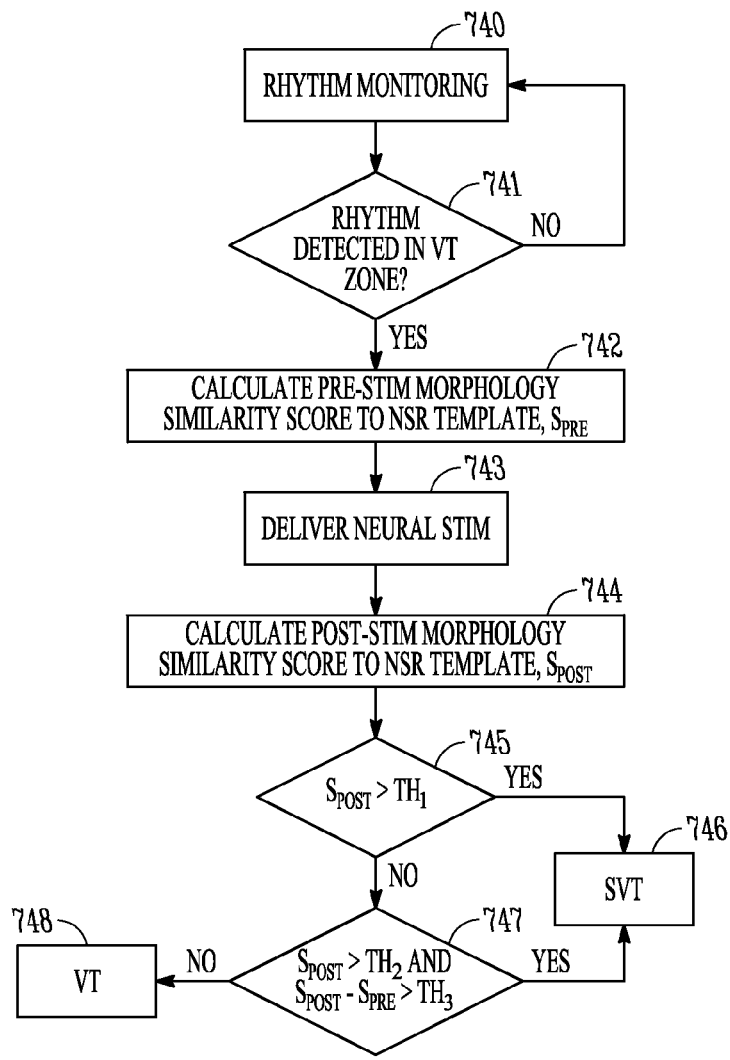
FIG. 7 illustrates an embodiment of a method for using ventricular morphology to discriminate between SVT and VT.

FIG. 7 illustrates an embodiment of a method for using ventricular morphology to discriminate between SVT and VT. A cardiac rhythm is monitored at 740. If the monitored rhythm is within a VT zone 741, then a pre-stimulation morphology is compared to a NSR template to determine a similarity score ($S_{PRE}$) at 742 in anticipation for the diagnostic neural stimulation. The diagnostic neural stimulation is delivered at 743, and the post-stimulation morphology is compared to the NSR template ($S_{POST}$) to determine a similarity score at 744, representing a time when the diagnostic neural stimulation is delivered and the AV delay is lengthened. An example of a similarity score is a correlation coefficient. At 745, a discrimination function is applied to $S_{POST}$ to determine if the arrhythmia is a SVT 746. According to various embodiments, if $S_{POST} > TH_1$, then the arrhythmia is classified as an SVT. At 747, a discrimination function is applied to $S_{PRE}$ and $S_{POST}$ to determine if the arrhythmia is a SVT 746 or a VT 748. According to various embodiments, if $S_{POST} > TH_2$ and $S_{POST} - S_{PRE} > TH_3$, then the arrhythmia is classified as an SVT, or otherwise the arrhythmia is classified as a VT.

Some embodiments capable of being implemented by a single chamber device discriminate SVT and VT by comparing ventricular hemodynamics before neural stimulation to ventricular hemodynamics during neural stimulation. VNS during an SVT event provides a more significant improvement in hemodynamics than VNS during an VT event, because the VNS during the SVT event (particularly AF/AT) achieves rate control. The improvement in hemodynamics during AV nodal VNS during AF has been demonstrated (see Wallick D. et al., AM J Physiol Heart Circ Physiol 281: H1490-H1497, 2001; and Zhuang S. et al. Circulation, 2002, 106: 1853-1858). The AV nodal VNS during AF increases systolic blood pressure, left ventricle systolic pressure, the rate of increase in the pressure during a cardiac cycle, the rate of decrease in the pressure during a cardiac cycle, and stroke volume. For example, stroke volume changed from SV: 8.9+/−3.0 ml to 15.5+/−4.6 ml, p<0.025) when VNS was delivered.

Figure 8:
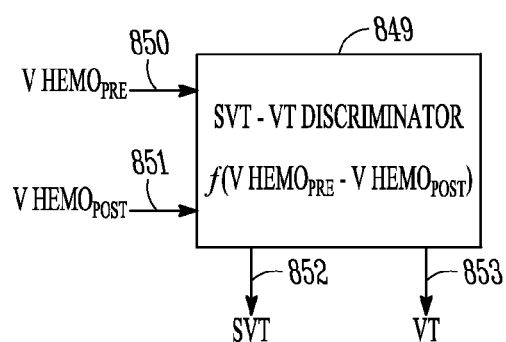
FIG. 8 illustrates an embodiment of a discriminator configured to discriminate between SVT and VT based on ventricular hemodynamics.

FIG. 8 illustrates an embodiment of a discriminator configured to discriminate between SVT and VT based on ventricular hemodynamics. The illustrated discriminator 849 has two inputs and two outputs. In the illustrated embodiment, a first input 850 provides a ventricular hemodynamic measure before neural stimulation (V $HEMO_{PRE}$) and a second input 851 provides a ventricular hemodynamic measure (V $HEMO_{POST}$) during neural stimulation. The discriminator performs a function ($f$(V $HEMO_{PRE}$, V $HEMO_{POST}$)) based on the ventricular hemodynamic measure to determine if the arrhythmia is an SVT 852 or a VT 853.

Additionally, sensor responses to the neural stimulation may be used to discriminate among arrhythmias. By way of example, LV impedance or LV-RV impedance may be used. The sensor responses are indicative of pressure change or stroke volume. The sensor response is measured before the neural stimulation and during the stimulation to differentiate SVT/VT and to differentiate SVT/AF. An arrhythmia is categorized as an SVT/AF if the pressure change or stroke volume is improved following VNS. If the improvement is not significant, then the arrhythmia is categorized as a VT.

Various embodiments can be implemented using a dual chamber device. Such devices are capable of providing additional information, such an atrial rate change in response to the neural stimulation, AV synchrony information such as may be obtained by comparing ventricular and atrial rates (V>A, or V−A rate difference), and the timing relationship between atrial and ventricular contraction, as AV nodal VNS extends the AV delay). For example, VNS during ST is typically associated with a slower atrial rate than VNS during reentrant SVT, as both atrial and ventricular rate are reduced and the AV delay is extended. VNS during AT/AFL does not significantly affect the atrial rate, but reduces ventricular rate. The reduced ventricular rate remains regular. Neural stimulation during AF does not significantly affect the atrial rate, but reduces the ventricular rate. The ventricular rate regularity improves because of the neural stimulation.

Furthermore, the arrhythmia may be classified as a 1:1 SVT (e.g. AVRT, AVNRT), where the atrial and ventricular rates are both reduced during the neural stimulation, but the 1:1 relationship between the atrial and ventricular activity is maintained. Also, the AV delay may be extended. The arrhythmia may be classified as a 1:1 retrograde VT, where the ventricular rate is not affected by the neural stimulation but the atrial rate is reduced (1:1 changed to V>A). The arrhythmia may be classified as a dual tachycardia such as AT and VT, or AF and VT or AFL and VT. The neural stimulation does not affect either the atrial rate or the ventricular rate.

Some embodiments use other discriminators along with the cardiac response to the neural stimulation delivered during the arrhythmia. Examples of such discriminators include sudden onset, stability, AV relationship and morphology. U.S. patent application Ser. No. 12/535,332, filed on Aug. 4, 2009, published as US 2010/0036447A1 on Feb. 11, 2010, and entitled "Neural Stimulation For Arrhythmia Recognition and Therapy" includes some examples of other discriminators, and is incorporated by reference herein in its entirety. A variety of therapies may be implemented to treat the arrhythmia. VNS, although used for discrimination, may terminate SVTs. Detected VTs may be treated by an antitachycardia therapy such as antitachycardia pacing or shocks. VNS may be used as rate-control therapy for AF or AFL, and VNS may be used together with other device-based or medical therapy for various SVT. Better recognition of SVT and VT leads to improved therapy delivery, as it reduces inappropriate anti-VT/VF therapy. Some SVTs are hemodynamically significant. Neural stimulation may be delivered as an SVT therapy. U.S. patent application Ser. No. 11/382,120, filed May 8, 2006, published as US 2007/0260283A1 on Nov. 8, 2007, and entitled "Method and Device for Providing Anti-Tachyarrhythmia Therapy" includes some examples of arrhythmia therapies, and is incorporated by reference herein in its entirety.

Figure 9:
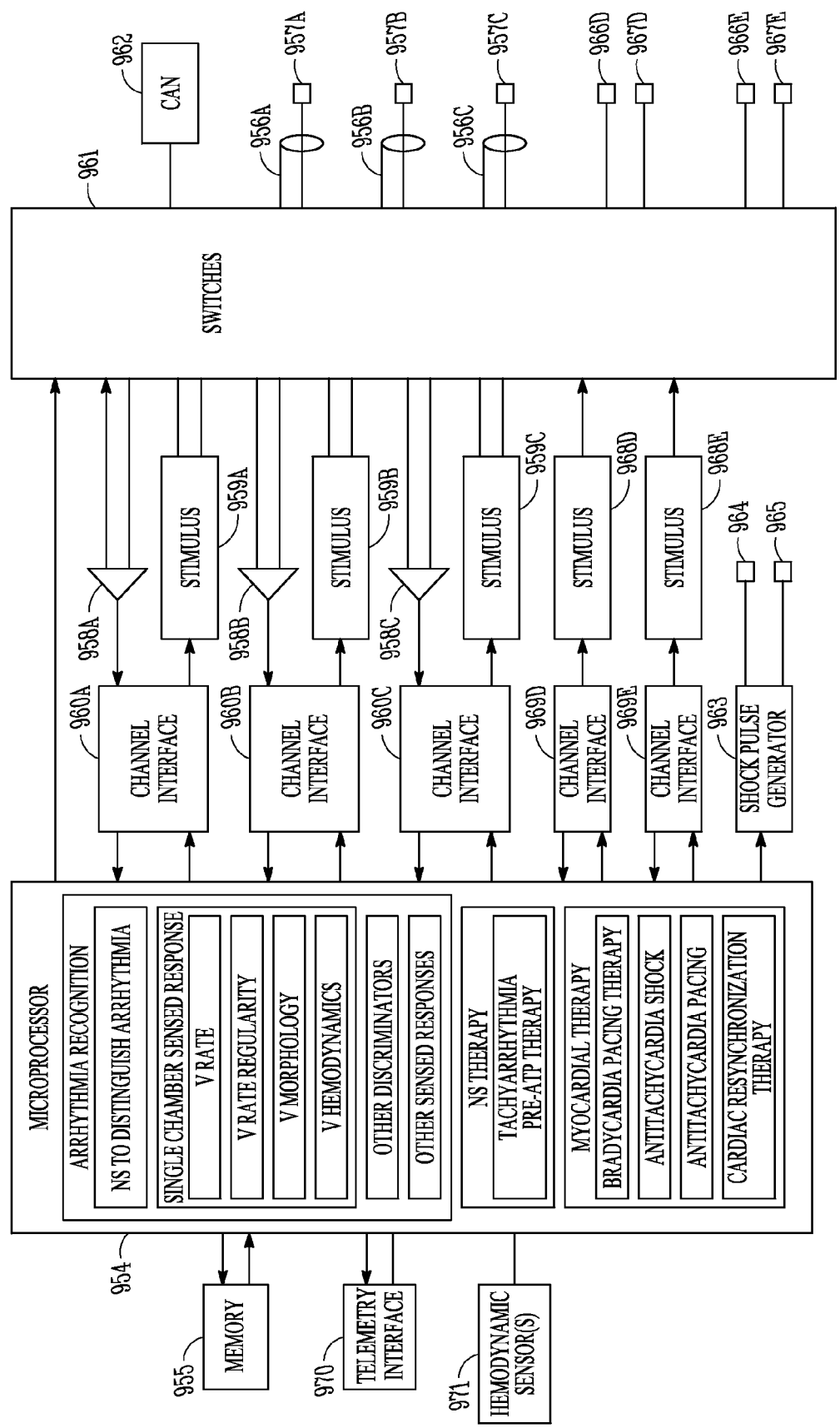
FIG. 9 shows a system diagram of an embodiment of a microprocessor-based implantable device, according to various embodiments.

FIG. 9 shows a system diagram of an embodiment of a microprocessor-based implantable device, according to various embodiments. The controller of the device is a microprocessor 954 which communicates with a memory 955 via a bidirectional data bus. The controller could be implemented by other types of logic circuitry (e.g., discrete components or programmable logic arrays) using a state machine type of design. As used herein, the term "circuitry" should be taken to refer to either discrete logic circuitry or to the programming of a microprocessor. Shown in the figure are three examples of sensing and pacing channels designated "A" through "C" comprising bipolar leads with ring electrodes 956A-C and tip electrodes 957A-C, sensing amplifiers 958A-C, pulse generators 959A-C, and channel interfaces 960A-C. Each channel thus includes a pacing channel made up of the pulse generator connected to the electrode and a sensing channel made up of the sense amplifier connected to the electrode. The channel interfaces 960A-C communicate bidirectionally with microprocessor 954, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect atrial and ventricular tachyarrhythmias.

The electrodes of each bipolar lead are connected via conductors within the lead to a switching network 961 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing (can) 962 or an electrode on another lead serving as a ground electrode. A shock pulse generator 963 is also interfaced to the controller for delivering a defibrillation shock via a pair of shock electrodes 964 and 965 and/or other electrodes to the atria or ventricles upon detection of a shockable tachyarrhythmia.

The controller may be programmed with a plurality of selectable ATP pacing protocols that define the manner in which anti-tachycardia pacing is delivered. In a microprocessor-based device, the output of pacing pulses can be controlled by a pacing routine that implements the selected pacing protocol as defined by various parameters. A data structure stored in memory contains the parameter sets that define each of the available pacing protocols. Different protocols are apt to be more successful than others in terminating particular tachyarrhythmias that may differ as to rate and/or depolarization pattern. Some devices are capable of employing a number of different ATP protocols to deliver therapy.

Neural stimulation channels, identified as channels D and E, are incorporated into the device for delivering parasympathetic stimulation and/or sympathetic inhibition, where one channel includes a bipolar lead with a first electrode 966D and a second electrode 967D, a pulse generator 968D, and a channel interface 969D, and the other channel includes a bipolar lead with a first electrode 966E and a second electrode 967E, a pulse generator 968E, and a channel interface 969E. Other embodiments may use unipolar leads in which case the neural stimulation pulses are referenced to the can or another electrode. The pulse generator for each channel outputs a train of neural stimulation pulses which may be varied by the controller as to amplitude, frequency, duty-cycle, and the like. In this embodiment, each of the neural stimulation channels uses a lead which can be intravascularly disposed near an appropriate stimulation site, e.g., near a baroreceptor in the case of a sympathetic inhibition channel or near a parasympathetic nerve in the case of a parasympathetic stimulation channel. Other types of leads and/or electrodes may also be employed. A nerve cuff electrode may be used in place of an intravascularly disposed electrode to provide neural stimulation, where the electrode may be placed, for example, around the cervical vagus nerve bundle to provide parasympathetic stimulation or around the aortic or carotid sinus nerve to provide sympathetic inhibition. Baroreceptors in or near the pulmonary artery may also be stimulated. In another embodiment, the leads of the neural stimulation electrodes are replaced by wireless links, and the electrodes for providing parasympathetic stimulation and/or sympathetic inhibition are incorporated into satellite units.

The figure illustrates a telemetry interface 970 connected to the microprocessor, which can be used to communicate with an external device. Some embodiments, as illustrated in the figure, also include a hemodynamic sensor or sensors 971 used to distinguish arrhythmias. The illustrated microprocessor 954 is capable of performing neural stimulation therapy routines and myocardial stimulation routines. Examples of NS therapy routines include a pre-ATP NS therapy for a tachyarrhythmia. Examples of myocardial therapy routines include bradycardia pacing therapies, anti-tachycardia shock therapies such as cardioversion or defibrillation therapies, anti-tachycardia pacing therapies, and cardiac resynchronization therapies. The illustrated micro controller also includes an arrhythmia recognition routine, which includes instructions for delivering diagnostic neural stimulation to distinguish arrhythmias, single chamber (e.g. right ventricle) sensed responses such as ventricular rate, ventricular rate regularity, ventricular morphology, and/or ventricular hemodynamics. Some embodiments also implement other discriminators and other sensed responses to distinguish between different types of arrhythmias.

Figure 10:
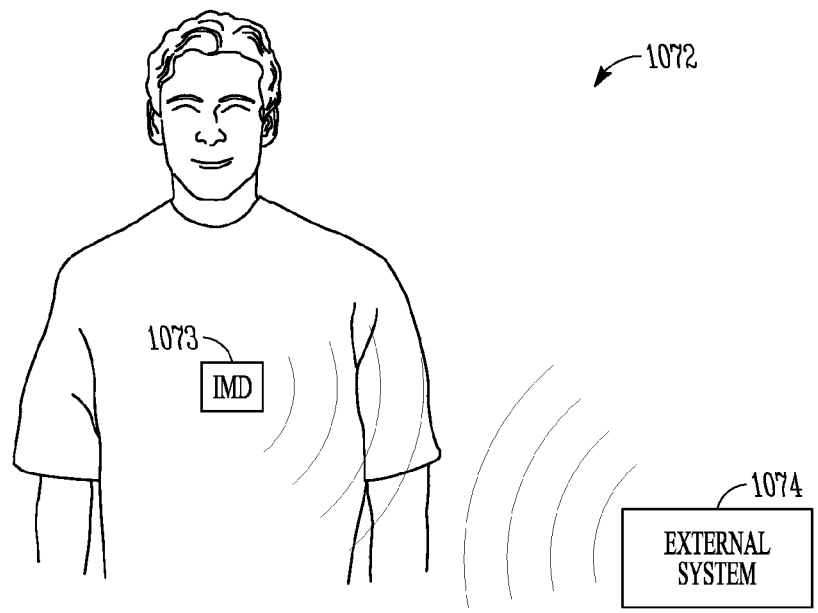
FIG. 10 illustrates a system including an implantable medical device (IMD) and an external system or device, according to various embodiments of the present subject matter.

FIG. 10 illustrates a system 1072 including an implantable medical device (IMD) 1073 and an external system or device 1074, according to various embodiments of the present subject matter. Various embodiments of the IMD include a combination of NS and CRM functions. The IMD may also deliver biological agents and pharmaceutical agents. The external system and the IMD are capable of wirelessly communicating data and instructions. In various embodiments, for example, the external system and IMD use telemetry coils to wirelessly communicate data and instructions. Thus, the external device (e.g. programmer) can be used to adjust the programmed therapy provided by the IMD, and the IMD can report device data (such as battery and lead resistance) and therapy data (such as sense and stimulation data) to the programmer using radio telemetry, for example. According to various embodiments, the IMD stimulates a neural target and/or myocardium to provide an anti-tachycardia therapy.

The external system allows a user such as a physician or other caregiver or a patient to control the operation of IMD and obtain information acquired by the IMD. In one embodiment, external system includes a programmer communicating with the IMD bi-directionally via a telemetry link. In another embodiment, the external system is a patient management system including an external device communicating with a remote device through a telecommunication network. The external device is within the vicinity of the IMD and communicates with the IMD bi-directionally via a telemetry link. The remote device allows the user to monitor and treat a patient from a distant location. The patient monitoring system is further discussed below.

The telemetry link provides for data transmission from the implantable medical device to the external system. This includes, for example, transmitting real-time physiological data acquired by the IMD, extracting physiological data acquired by and stored in the IMD, extracting therapy history data stored in implantable medical device, and extracting data indicating an operational status of the IMD (e.g., battery status and lead impedance). The telemetry link also provides for data transmission from the external system to the IMD. This includes, for example, programming the IMD to acquire physiological data, programming IMD to perform at least one self-diagnostic test (such as for a device operational status), and programming the IMD to deliver at least one therapy.

Figure 11:
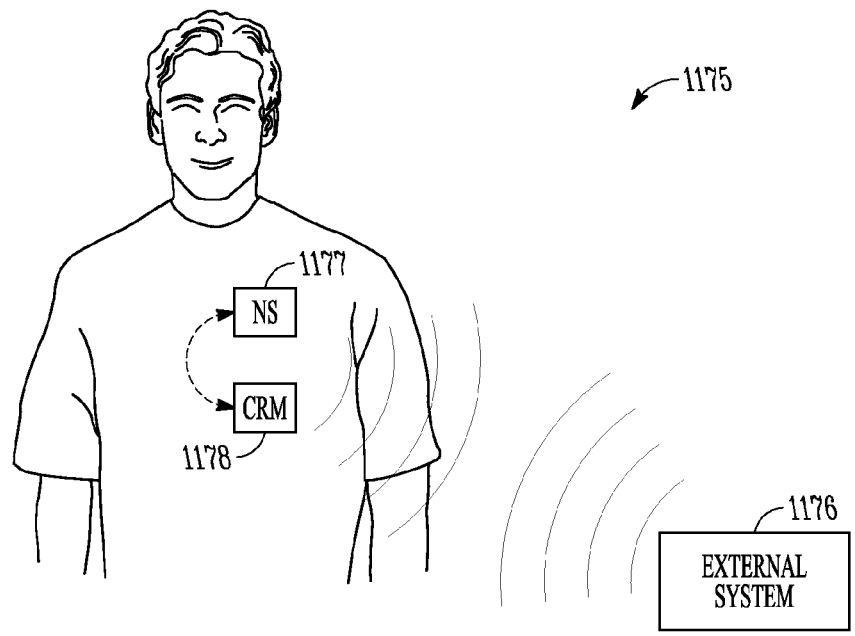
FIG. 11 illustrates a system including an external device, an implantable neural stimulator (NS) device and an implantable cardiac rhythm management (CRM) device, according to various embodiments of the present subject matter.

FIG. 11 illustrates a system 1175 including an external device 1176, an implantable neural stimulator (NS) device 1177 and an implantable cardiac rhythm management (CRM) device 1178, according to various embodiments of the present subject matter. Various aspects involve a method for communicating between a NS device and a CRM device or other cardiac stimulator. In various embodiments, this communication allows one of the devices 1178 or 1178 to deliver more appropriate therapy (i.e. more appropriate NS therapy or CRM therapy) based on data received from the other device. Some embodiments provide on-demand communications. In various embodiments, this communication allows each of the devices to deliver more appropriate therapy (i.e. more appropriate NS therapy and CRM therapy) based on data received from the other device. The illustrated NS device and the CRM device are capable of wirelessly communicating with each other, and the external system is capable of wirelessly communicating with at least one of the NS and the CRM devices. For example, various embodiments use telemetry coils to wirelessly communicate data and instructions to each other. In other embodiments, communication of data and/or energy is by ultrasonic means. Rather than providing wireless communication between the NS and CRM devices, various embodiments provide a communication cable or wire, such as an intravenously-fed lead, for use to communicate between the NS device and the CRM device. In some embodiments, the external system functions as a communication bridge between the NS and CRM devices.

Figure 12:
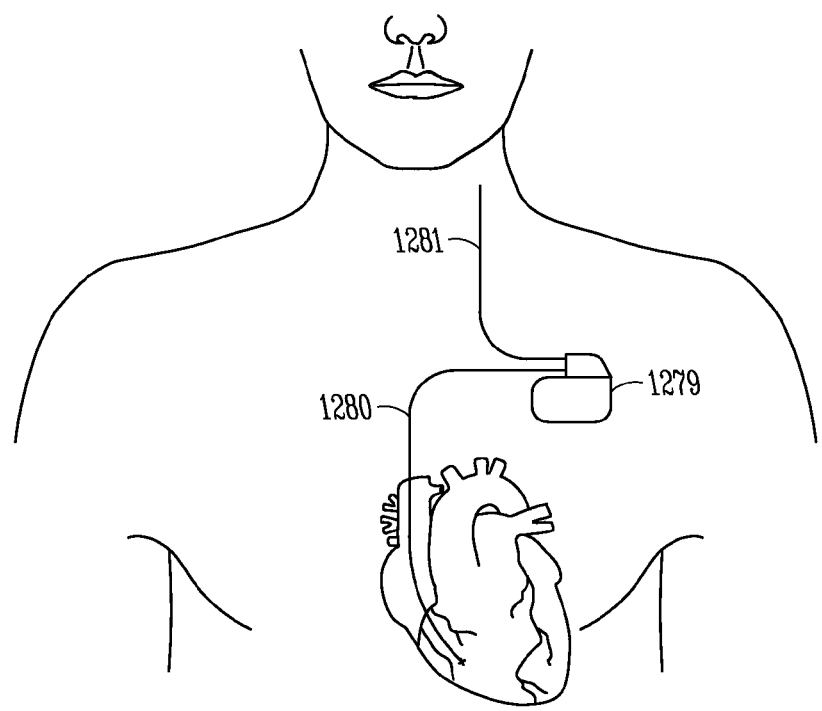
FIG. 12 illustrates an IMD placed subcutaneously or submuscularly in a patient's chest with lead(s) positioned to sense ventricular activity, and with lead(s) positioned to stimulate a left vagus nerve, by way of example and not by way of limitation, according to various embodiments.

FIG. 12 illustrates an IMD 1279 placed subcutaneously or submuscularly in a patient's chest with lead(s) 1280 positioned to sense ventricular activity (e.g. right ventricular activity), and with lead(s) 1281 positioned to stimulate a vagal neural target (e.g. left vagal nerve), by way of example and not by way of limitation, according to various embodiments. The left vagus nerve innervates the AV node, and thus can be used to deliver the diagnostic neural stimulation to discriminate between or among arrhythmias. The right ventricle lead can be used to discriminate arrhythmias from the right ventricle. Other leads may be included.

Figure 13:
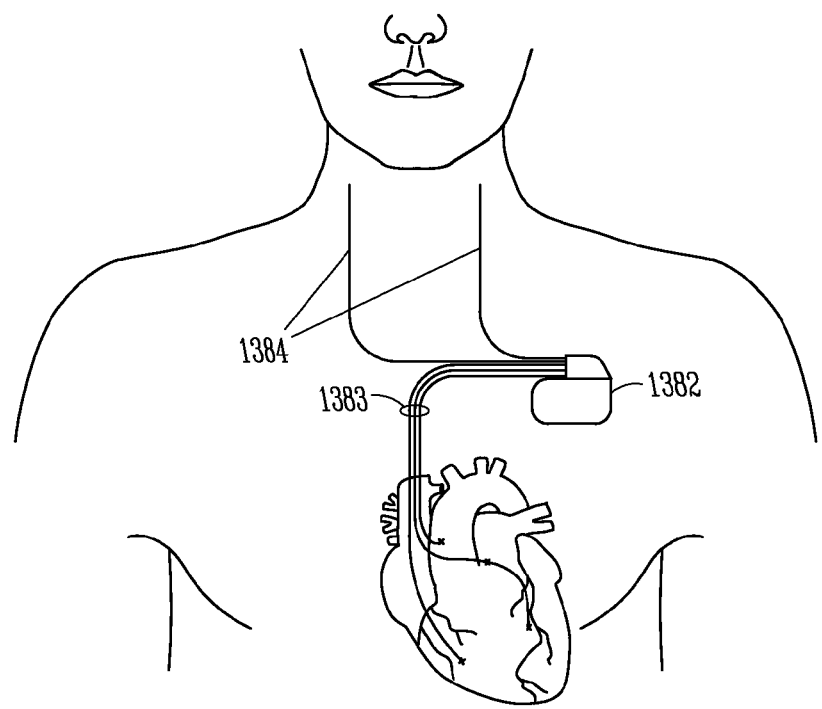
FIG. 13 illustrates an IMD placed subcutaneously or submuscularly in a patient's chest with lead(s) positioned to provide a CRM therapy to a heart, and with lead(s) positioned to deliver vagal stimulation, by way of example and not by way of limitation, according to various embodiments.

For example, FIG. 13 illustrates an IMD 1382 placed subcutaneously or submuscularly in a patient's chest with lead(s) 1383 positioned to provide a CRM therapy to a heart, and with lead(s) 1384 positioned to deliver VNS, by way of example and not by way of limitation, according to various embodiments. The leads 1383 can be used to deliver ATP and/or shock therapy. According to various embodiments, the leads 1383 are positioned in or proximate to the heart to provide a desired cardiac pacing therapy. In some embodiments, the lead(s) 1383 are positioned in or proximate to the heart to provide a desired CRT therapy. Some embodiments place the leads in positions with respect to the heart that enable the lead(s) to deliver the combinations of at least two of the pacing, defibrillation and CRT therapies. According to various embodiments, neural stimulation lead(s) 1384 are subcutaneously tunneled to a neural target, and can have a nerve cuff electrode to stimulate the neural target. Some lead embodiments are intravascularly fed into a vessel proximate to the neural target, and use transducer(s) within the vessel to transvascularly stimulate the neural target. For example, some embodiments stimulate the vagus nerve using electrode(s) positioned within the internal jugular vein.

Figure 14:
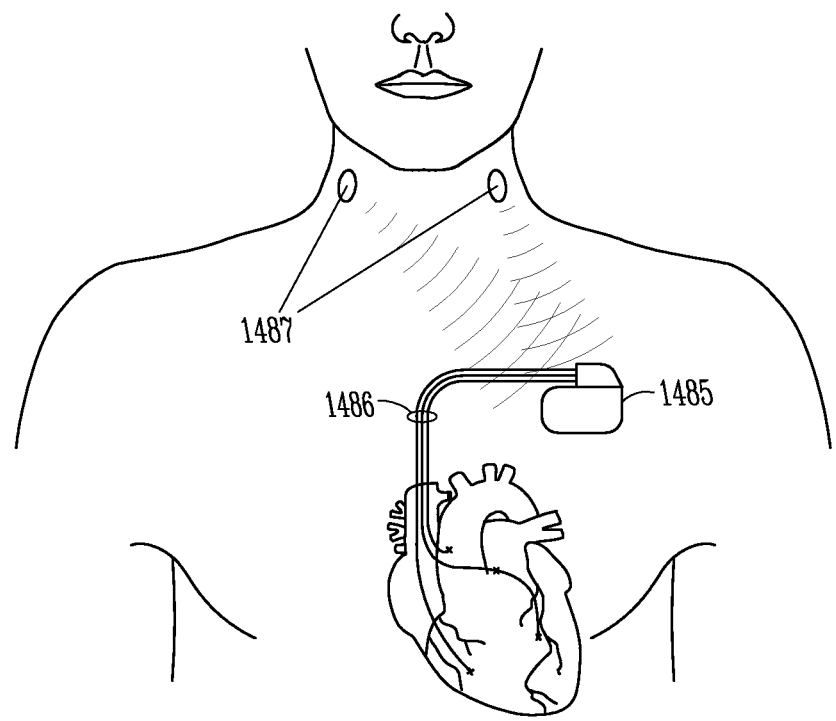
FIG. 14 illustrates an IMD with lead(s) positioned to provide a CRM therapy to a heart, and with satellite transducers positioned to stimulate at least one parasympathetic neural target as part of a myocardium conditioning therapy, according to various embodiments.

FIG. 14 illustrates an IMD 1485 with lead(s) 1486 positioned to provide a CRM therapy to a heart, and with satellite transducers 1487 positioned to stimulate at least one parasympathetic neural target, according to various embodiments. The satellite transducers are connected to the IMD, which functions as the planet for the satellites, via a wireless link. Stimulation and communication can be performed through the wireless link. Examples of wireless links include RF links and ultrasound links. Although not illustrated, some embodiments perform myocardial stimulation using wireless links. Examples of satellite transducers include subcutaneous transducers, nerve cuff transducers and intravascular transducers.

One of ordinary skill in the art will understand that, the modules and other circuitry shown and described herein can be implemented using software, hardware, firmware and combinations of software and hardware.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods are implemented using a sequence of instructions which, when executed by one or more processors, cause the processor(s) to perform the respective method. In various embodiments, the methods are implemented as a set of instructions contained on a computer-accessible medium such as a magnetic medium, an electronic medium, or an optical medium.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method for classifying and treating an arrhythmia, comprising:
    implementing a programmed arrhythmia recognition routine to classify the arrhythmia before treating the arrhythmia, wherein implementing the programmed arrhythmia recognition includes:
        sensing a characteristic of a ventricle before delivering a diagnostic neural stimulation;
        delivering the diagnostic neural stimulation to diagnose the arrhythmia;
        sensing the characteristic of the ventricle while delivering the diagnostic neural stimulation; and
        using the sensed characteristic of the ventricle before and during the diagnostic neural stimulation to classify the arrhythmia as either a supraventricular tachyarrhythmia (SVT) or a ventricular tachycardia (VT); and
    implementing a programmed response to classifying the arrhythmia after completing the programmed arrhythmia recognition routine, including:
        delivering a VT therapy to treat the VT when the classified arrhythmia is the VT; and
        either delivering no therapy or delivering an SVT therapy to treat the SVT when the classified arrhythmia is the SVT,
    wherein:
        the VT therapy and the SVT therapy each have distinct protocols from the diagnostic neural stimulation and are delivered after completion of the programmed arrhythmia recognition routine; and
        the SVT therapy includes myocardial stimulation therapy.

2. The method of claim 1, wherein:
    sensing the characteristic of the ventricle before delivering the diagnostic neural stimulation includes sensing a ventricular rate before delivering the diagnostic neural stimulation;
    sensing the characteristic of the ventricle while delivering the diagnostic neural stimulation includes sensing the ventricular rate while delivering the diagnostic neural stimulation; and
    using the sensed characteristic of the ventricle before and during the diagnostic neural stimulation to classify the arrhythmia includes using the ventricular rate before and during the diagnostic neural stimulation to classify the arrhythmia as either the SVT or the VT.

3. The method of claim 2, wherein using the ventricular rate before and during the diagnostic neural stimulation to classify the arrhythmia as either the SVT or the VT includes:
    determining a change in the ventricular rate between the ventricular rate before and during the diagnostic neural stimulation;
    determining if the change in the ventricular rate is more than a threshold; and
    classifying the arrhythmia as the SVT when the change in the ventricular rate is more than the threshold.

4. The method of claim 3, wherein:
    the change in the ventricular rate includes a percent change in the ventricular rate from the ventricular rate before the diagnostic neural stimulation;
    the threshold includes a percent change threshold; and
    determining if the change in the ventricular rate is more than a threshold includes determining if the percent change in the ventricular rate is more than the percent change threshold.

5. The method of claim 2, wherein:
    sensing the characteristic of the ventricle before delivering the diagnostic neural stimulation further includes sensing a ventricular rate regularity before delivering the diagnostic neural stimulation;
    sensing the characteristic of the ventricle while delivering the diagnostic neural stimulation further includes sensing the ventricular rate regularity while delivering the diagnostic neural stimulation; and
    using the sensed characteristic of the ventricle before and during the diagnostic neural stimulation to classify the arrhythmia further includes, when the arrhythmia is classified as the SVT, using the ventricular rate regularity before and during the diagnostic neural stimulation to classify the SVT as atrial fibrillation (AF) or as another SVT.

6. The method of claim 5, wherein using the ventricular rate regularity before and during the diagnostic neural stimulation to classify the SVT as either the AF or another SVT includes:
    determining a change in the ventricular rate regularity between the characteristic of the ventricle before and during the diagnostic neural stimulation;
    determining if the change in the ventricular rate regularity is more than a threshold; and
    classifying the arrhythmia as the AF when the change is more than the threshold.

7. The method of claim 6, wherein:
    the change in the ventricular rate regularity includes a percent change in the ventricular rate regularity from the characteristic of the ventricle before the diagnostic neural stimulation;
    the threshold includes a percent change threshold; and
    determining if the change in the ventricular rate regularity is more than a threshold includes determining if the percent change in the ventricular rate regularity is more than the percent change threshold.

8. The method of claim 1, wherein:
sensing the characteristic of the ventricle before delivering the diagnostic neural stimulation includes sensing a ventricular morphology before delivering the diagnostic neural stimulation and comparing the sensed ventricular morphology to a normal sinus rhythm (NSR) to determine a similarity value ($S_{PRE}$);
sensing the characteristic of the ventricle while delivering the diagnostic neural stimulation includes sensing a ventricular morphology while delivering the diagnostic neural stimulation and comparing the sensed ventricular morphology to the NSR to determine a similarity value ($S_{POST}$); and
using the sensed characteristic of the ventricle before and during the diagnostic neural stimulation to classify the arrhythmia includes using the $S_{PRE}$ and the $S_{POST}$ to classify the arrhythmia as either the SVT or the VT.

9. The method of claim 8, wherein using the $S_{PRE}$ and the $S_{POST}$ to classify the arrhythmia as either the SVT or the VT includes classifying the arrhythmia as the SVT if $S_{POST}$ is greater than a first threshold ($TH_1$) or if the $S_{POST}$ is greater than a second threshold ($TH_2$) and the difference between $S_{POST}$ and $S_{PRE}$ is greater than a third threshold ($TH_3$).

10. The method of claim 1, wherein:
sensing the characteristic of the ventricle before delivering the diagnostic neural stimulation includes sensing ventricular hemodynamics (V $HEMO_{PRE}$) before delivering the diagnostic neural stimulation;
sensing the characteristic of the ventricle while delivering the diagnostic neural stimulation includes sensing ventricular hemodynamics (V $HEMO_{POST}$) while delivering the diagnostic neural stimulation; and
using the sensed characteristic of the ventricle before and during the diagnostic neural stimulation to classify the arrhythmia includes using V $HEMO_{PRE}$ and V $HEMO_{POST}$ to classify the arrhythmia as either the SVT or the VT.

11. The method of claim 1, wherein delivering the diagnostic neural stimulation includes transvascularly stimulating a vagus nerve or a cardiac branch of the vagus nerve.

12. The method of claim 1, wherein delivering the diagnostic neural stimulation includes stimulating a baroreflex response.

13. A system for classifying and treating an arrhythmia, comprising:
an arrhythmia discriminator configured to discriminate between ventricular tachycardia (VT) and supraventricular tachycardia (SVT);
a neural stimulator configured to generate a neural stimulation signal and deliver the neural stimulation signal to an autonomic neural target;
a therapy delivery circuit configured to generate therapy to treat the arrhythmia; and
a controller operably connected to the arrhythmia discriminator, the therapy delivery circuit and the neural stimulator, wherein the controller is configured to implement a programmed arrhythmia recognition routine to classify the arrhythmia, and then after completing the programmed arrhythmia recognition routine implement a programmed response to classifying the arrhythmia, wherein:
to implement the programmed arrhythmia recognition routine, the controller is configured to control the neural stimulator to deliver a diagnostic neural stimulation for diagnosing the arrhythmia, to determine a ventricle characteristic before the diagnostic neural stimulation and to determine a ventricle characteristic during the diagnostic neural stimulation, to classify the arrhythmia as either the SVT or the VT based on the ventricle characteristic before the diagnostic neural stimulation and the ventricle characteristic during the diagnostic neural stimulation; and
to implement the programmed response after completing the programmed arrhythmia recognition routine, the controller is configured to deliver a VT therapy to treat the VT when the classified arrhythmia is the VT, and to deliver an SVT therapy to treat the SVT when the classified arrhythmia is the SVT,
wherein:
the VT therapy and the SVT therapy each have distinct protocols from the diagnostic neural stimulation; and
the SVT therapy includes myocardial stimulation therapy.

14. The system of claim 13, wherein:
the ventricle characteristic before delivering the diagnostic neural stimulation includes a ventricular rate before delivering the diagnostic neural stimulation;
the ventricle characteristic while delivering the diagnostic neural stimulation includes the ventricular rate while delivering the diagnostic neural stimulation; and
the controller is configured to classify the arrhythmia using the ventricular rate before and the ventricular rate during the diagnostic neural stimulation to classify the arrhythmia as either the SVT or the VT.

15. The system of claim 14, wherein the controller is configured to:
determine a change in the ventricular rate between the ventricular rate before and during the diagnostic neural stimulation;
determine if the change in the ventricular rate is more than a threshold; and
classify the arrhythmia as the SVT when the change in the ventricular rate is more than the threshold.

16. The system of claim 15, wherein:
the change in the ventricular rate includes a percent change in the ventricular rate from the ventricular rate before the diagnostic neural stimulation;
the threshold includes a percent change threshold; and
the controller is configured to determine if the percent change in the ventricular rate more than the percent change threshold.

17. The system of claim 14, wherein:
the ventricle characteristic before delivering the diagnostic neural stimulation further includes a ventricular rate regularity before delivering the diagnostic neural stimulation;
the ventricle characteristic while delivering the diagnostic neural stimulation further includes the ventricular rate regularity while delivering the diagnostic neural stimulation; and
the controller is configured to use the ventricular rate regularity before and during the diagnostic neural stimulation to classify the SVT as either atrial fibrillation (AF) or as another SVT.

18. The system of claim 17, wherein the controller is configured to:
determine a change in the ventricular rate regularity between the ventricle characteristic before and during the diagnostic neural stimulation;
determine if the change in the ventricular rate regularity is more than a threshold; and
classify the SVT as the AF when the change is more than the threshold.

19. The system of claim 18, wherein:
the change in the ventricular rate regularity includes a percent change in the ventricular rate regularity from the characteristic of the ventricle before the diagnostic neural stimulation;
the threshold includes a percent change threshold; and the controller is configured to determine if the percent change in the ventricular rate regularity is more than the percent change threshold.

20. The system of claim 13, wherein the controller is configured to determine a similarity value ($S_{PRE}$) of a ventricular morphology before delivering the diagnostic neural stimulation to a normal sinus rhythm (NSR) template, determine a similarity value ($S_{POST}$) of a ventricular morphology during delivering the diagnostic neural stimulation to the NSR template, and use the $S_{PRE}$ and the $S_{POST}$ to classify the arrhythmia as either the SVT or the VT.

21. The system of claim 20, wherein the controller is configured to classify the arrhythmia as the SVT if $S_{POST}$ is greater than a first threshold ($TH_1$), or if the $S_{POST}$ is greater than a second threshold ($TH_2$) and the difference between $S_{POST}$ and $S_{PRE}$ is greater than a third threshold ($TH_3$).

22. The system of claim 13, further comprising sensors configured to sense ventricular hemodynamics, wherein the controller is configured to use ventricular hemodynamics (V $HEMO_{PRE}$) before delivering the diagnostic neural stimulation and ventricular hemodynamics (V $HEMO_{POST}$) while delivering the diagnostic neural stimulation to classify the arrhythmia as either the SVT or the VT.

* * * * *